US009161818B2

(12) United States Patent
Arthur et al.

(10) Patent No.: US 9,161,818 B2
(45) Date of Patent: Oct. 20, 2015

(54) DEVICE FOR PERFORMING A SURGICAL PROCEDURE AND METHOD

(71) Applicant: KYPHON SARL, Neuchatel (CH)

(72) Inventors: Amy L. Arthur, Mountain View, CA (US); Neil S. Sasaki, Santa Clara, CA (US)

(73) Assignee: KYPHON SARL, Neuchatel (CH)

( * ) Notice: Subject to any disclaimer, the term of this patent is extended or adjusted under 35 U.S.C. 154(b) by 237 days.

(21) Appl. No.: 13/798,320

(22) Filed: Mar. 13, 2013

(65) Prior Publication Data

US 2014/0277209 A1    Sep. 18, 2014

(51) Int. Cl.

| A61B 17/58 | (2006.01) |
| A61B 19/00 | (2006.01) |
| A61B 17/15 | (2006.01) |
| A61B 17/88 | (2006.01) |

(52) U.S. Cl.
CPC ............... *A61B 19/26* (2013.01); *A61B 17/15* (2013.01); *A61B 17/8816* (2013.01); *A61B 17/8855* (2013.01); *A61B 19/20* (2013.01); *A61B 19/201* (2013.01); *A61B 2019/267* (2013.01)

(58) Field of Classification Search
CPC ............................... A61B 19/20; A61B 19/201
See application file for complete search history.

(56) References Cited

U.S. PATENT DOCUMENTS

| 2,697,433 | A | * | 12/1954 | Zehnder | 606/96 |
| 3,017,887 | A | * | 1/1962 | Heyer | 604/175 |
| 3,021,842 | A | * | 2/1962 | Flood | 604/175 |
| 3,055,370 | A | * | 9/1962 | McKinney et al. | 606/129 |
| 4,809,694 | A | * | 3/1989 | Ferrara | 606/130 |
| 5,263,956 | A | * | 11/1993 | Nobles | 606/130 |
| 5,405,330 | A | | 4/1995 | Zunitch et al. | |
| 5,681,325 | A | | 10/1997 | Hasson | |
| 5,810,712 | A | | 9/1998 | Dunn | |
| 5,865,817 | A | | 2/1999 | Moenning et al. | |
| 6,039,725 | A | | 3/2000 | Moenning et al. | |
| 6,110,182 | A | | 8/2000 | Mowlai-Ashtiani | |
| 6,287,281 | B1 | | 9/2001 | Nishtala et al. | |
| 6,488,664 | B1 | | 12/2002 | Solomon et al. | |
| 6,527,782 | B2 | * | 3/2003 | Hogg et al. | 606/130 |

* cited by examiner

*Primary Examiner* — Nicholas Woodall
(74) *Attorney, Agent, or Firm* — Sorell Lenna & Schmidt LLP

(57) ABSTRACT

A device for holding a surgical tool includes a first member extending along a longitudinal axis between a first end and a second end. The first end includes an inner surface defining a conduit extending transverse to the longitudinal axis. The conduit includes a first portion and a second portion defining a first chamber. A cap has an inner surface including a first section configured to engage an outer surface of the first member and a second section defining a second chamber extending transverse to the longitudinal axis. The second chamber is in communication with the first chamber when the cap engages the first member such that the first and second chambers define a cavity. A pivoting member is movably disposed in the cavity and includes an inner surface defining a passageway. A second member is disposed within the passageway. Methods of use are disclosed.

15 Claims, 2 Drawing Sheets

DEVICE FOR PERFORMING A SURGICAL PROCEDURE AND METHOD

TECHNICAL FIELD

The present disclosure generally relates to medical devices for the treatment of musculoskeletal structures, and more particularly to a surgical system and method that include a device configured to hold a surgical instrument while a surgical procedure is performed.

BACKGROUND

Height loss is commonly associated with fractures, such as, for example, spinal fractures, typically referred to as vertebral compression fractures. A large segment of osteoporotic patients experience vertebral compression fractures, with an estimated 700,000 such fractures occurring annually. Kyphoplasty is a minimally invasive procedure that is used to treat vertebral compression fractures using a combination of vertebroplasty utilizing a bone void filler, such as, for example, bone cement with balloon catheter technology. The kyphoplasty procedure restores height of the collapsed spinal bone which diminishes associated back pain.

Kyphoplasty procedures may also be used to treat fractures in other areas of a patient's body, such as, for example, a distal radius of the patient. To treat a distal radius fracture using a kyphoplasty procedure, an inflatable bone tamp (IBT) is utilized. The IBT is used to percutaneously reduce comminuted, articular depressions in a controlled manner. Fracture morphologies, such as, for example, "die-punch" fractures are especially suited for correction by an IBT. IBTs are deployed to a surgical site, such as, for example, a bone defect through a working cannula. IBTs create well-defined voids. After the void is created by the IBT, the IBT is removed from the cannula and a material, such as, for example a bone void filler is delivered through the cannula and into the void. The bone void filler may be used in conjunction with percutaneous pins, ex-fixes, screws and/or plates for fracture fixation.

In conventional kyphoplasty a procedure, the IBT is inserted adjacent the bone defects by inserting the IBT through a cannula. An inflatable member of the IBT is expanded to create a void in or adjacent the bone defect. After the IBT creates the void, the IBT is removed from the cannula and a bone void filler is delivered through the cannula to the void in order to at least partially fill the void. It is therefore important that the cannula be properly oriented with respect to the bone defect. In conventional kyphoplasty procedures, the cannula is held at a desired trajectory by a physician or physician's assistant, so that the IBT or bone void filler may be delivered through the cannula to a location adjacent the bone defect or void created by the IBT.

Percutaneous delivery of IBT or bone filler material through the cannula to a bone defect or bone void can be difficult. For example, the IBT or bone void filler material may get stuck in the cannula. Furthermore, the distal end of the cannula must be positioned adjacent to the bone defect or bone void to allow the IBT or bone void filler to be delivered through the cannula to the bone defect or bone void. There is often little soft tissue and/or bony anatomy to hold the cannula in a stable position during delivery of the IBT or bone filler material. To stabilize the cannula, a surgical assistant is often required to provide an extra pair of hands to hold the cannula while a surgeon delivers the IBT or the bone filler material to the bone defect or bone void through the cannula. The present disclosure provides a device that acts as a second pair of hands to hold the cannula at a fixed trajectory to ensure that the cannula is properly positioned relative to the bone defect or bone void. This disclosure describes an improvement over these prior art technologies.

SUMMARY

Accordingly, a surgical system and method for correction of a bone injury or disorder are provided. In one embodiment, in accordance with the principles of the present disclosure, the surgical system includes a device for performing a surgical procedure. The device comprises a first member extending along a longitudinal axis between a first end and a second end. The first end includes an inner surface defining a conduit extending transverse to the longitudinal axis. The conduit includes a first portion and a second portion defining a first chamber. A cap has an inner surface including a first section configured to engage an outer surface of the first member and a second section defining a second chamber extending transverse to the longitudinal axis. The second chamber is in communication with the first chamber when the cap engages the first member such that the first and second chambers define a cavity. A pivoting member is movably disposed in the cavity and includes an inner surface defining a passageway. A second member is disposed within the passageway.

In one embodiment, in accordance with the principles of the present disclosure, the surgical system includes a device comprising a first member extending along a longitudinal axis between a first end and a second end. The first end includes an inner surface defining a conduit extending transverse to the longitudinal axis. The conduit includes a first portion and a second portion defining a first chamber having a hemispherical configuration. The first portion is tapered between a first end and a second end, the second portion extending from the second end of the first portion. A cap has an inner surface including a threaded first section configured to engage a threaded outer surface of the first member and a second section defining a second chamber having a hemispherical configuration and extending transverse to the longitudinal axis. The second chamber is in communication with the first chamber when the cap engages the first member such that the first chamber is continuous with the second chamber and the first and second chambers define a spherical cavity. The second section includes a projection extending parallel to the longitudinal axis. A pivoting member is movably disposed in the cavity and includes an inner surface defining a passageway. The pivoting member includes a first end comprising a ball, a second end comprising a collet and a recess between the ball and the collet configured for disposal of the projection when the cap engages the first member. A second member is disposed within the passageway. The second member includes an inner surface defining a second passageway having an inflatable bone tamp or a bone void filler disposed therein.

In one embodiment, in accordance with the principles of the present disclosure, a method for repairing a bone is provided. The method comprises the steps of: providing a device comprising: a first member extending along a longitudinal axis between a first end and a second end, the first end including an inner surface defining a conduit extending transverse to the longitudinal axis, the conduit including a first portion and a second portion defining a first chamber, a cap having an inner surface including a first section configured to engage an outer surface of the first member and a second section defining a second chamber extending transverse to the longitudinal axis, the second chamber being in communication with the first chamber when the cap engages the first member such that the first and second chambers define a cavity, and a pivoting member movably disposed in the cavity and including an inner surface defining a passageway; creating an access path to a defect in a bone; inserting the second end of the first member through the access path; inserting a second member into the passageway; and engaging the cap with the first member.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
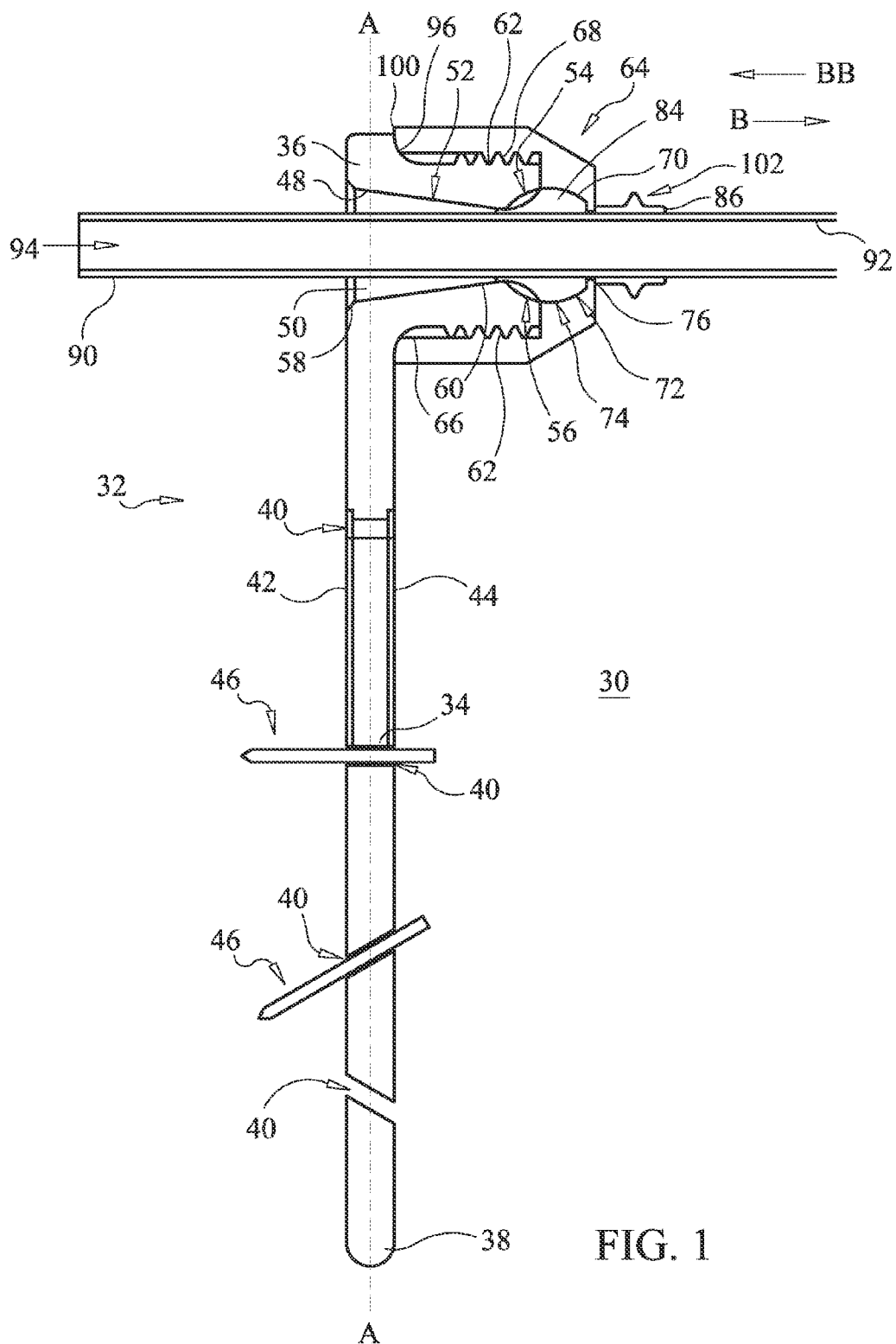
FIG. 1 is a side, cross sectional view of one embodiment of components of a system in accordance with the principles of the present disclosure.

The exemplary embodiments of the surgical system and related methods of use disclosed are discussed in terms of medical devices for the treatment of musculoskeletal disorders and more particularly, in terms of a surgical system and method for bone repair. It is envisioned that the surgical system and method may be employed in applications such as for correction of fractures, depressions and breaks. For example, the surgical system and method include a device configured to hold a surgical instrument while performing a surgical procedure to treat a bone defect, such as, for example a fracture.

In one embodiment, the system and method include a device including a ball and socket design. The ball includes a collet and a through hole extending through the ball and the collet configured for disposal of a surgical instrument, such as, for example, a cannula. The ball is configured to interface a socket in a tail of the device. A cap tightens around the collet to rigidly hold the cannula and to lock the ball in place relative to the socket. This configuration allows the cannula to be held at a fixed angle relative to the tail to prevent misplacement of the cannula. In some embodiments, at least a portion of the device is formed from silicone to hold the ball in the socket.

It is contemplated that one or all of the components of the surgical system may be disposable, peel-pack, pre-packed sterile devices. One or all of the components of the surgical system may be reusable. The surgical system may be configured as a kit with multiple sized and configured components, such as, for example, balloons that are preformed to have different sizes and shapes.

It is envisioned that the present disclosure may be employed to treat bones, such as, for example, spinal bones or arm bones. It should be understood that the present principles are applicable to any bone structures, including but not limited to bones of the spine, legs, feet, hands, etc. It is contemplated that the present disclosure may be employed with other osteal and bone related applications, including those associated with diagnostics and therapeutics. It is further contemplated that the disclosed surgical system and methods may alternatively be employed in a surgical treatment with a patient in a prone or supine position, and/or employ various surgical approaches, including anterior, posterior, posterior mid-line, direct lateral, postero-lateral, antero-lateral, etc. approaches in the arm, spine or other body regions. The present disclosure may also be alternatively employed with procedures for treating the muscles, ligaments, tendons or any other body part. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 2:
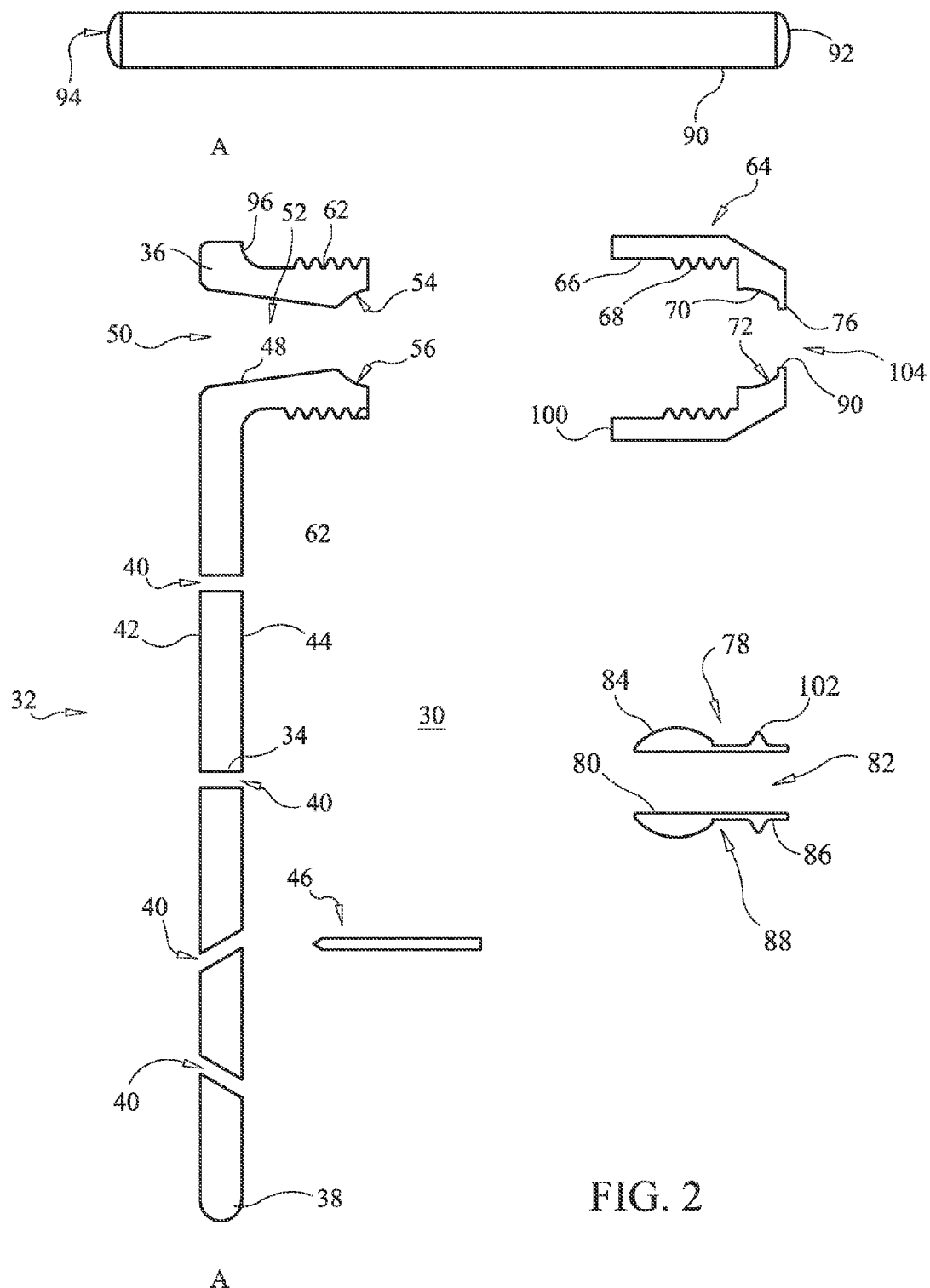
FIG. 2 is a side, cross sectional view of components of the system shown in FIG. 1, with parts separated.

The following disclosure includes a description of a surgical system for holding a surgical instrument while a surgical procedure is performed. The disclosure also includes a description of related methods of employing the disclosed surgical system. Alternate embodiments are also disclosed. Reference will now be made in detail to the exemplary embodiments of the present disclosure, which are illustrated in the accompanying figures. Turning now to FIGS. 1 and 2, there are illustrated components of a surgical system, such as, for example, a surgical system 30 and embodiments in accordance with the principles of the present disclosure.

The components of system 30 can be fabricated from biologically acceptable materials suitable for medical applications, including metals, synthetic polymers, ceramics and bone material and/or their composites, depending on the particular application and/or preference of a medical practitioner. For example, the components of system 30, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 30 may have material composites, including the above materials, to achieve various desired characteristics such as strength, rigidity, elasticity, compliance, biomechanical performance, durability and radiolucency or imaging preference. The components of system 30, individually or collectively, may also be fabricated from a heterogeneous material such as a combination of two or more of the above-described materials. The components of system 30 may be monolithically formed, integrally connected or include fastening elements and/or instruments, as described herein.

System 30 is employed, for example, with an open, mini-open or minimally invasive surgical technique to treat a bone defect, such as, for example a fracture. System 30 includes a device 32 having a tail, such as, for example, a first member 34 extending along a longitudinal axis A between a first end 36 and a second end 38. End 38 includes an opening 40 extending through a first surface 42 and an opposite surface 44. Opening 40 is configured to receive an engagement device, such as, for example a pin or K-wire 46 configured to fix device 32 relative to the anatomy of a patient. It is envisioned that end 38 may include one or a plurality of openings 40. It is further envisioned that system 30 may include one or a plurality of pins/K-wires 46, corresponding to the number of openings 40.

In the embodiment shown in FIGS. 1 and 2, end 38 includes openings 40 extending perpendicular to axis A positioned proximally of openings 40 extending at an acute angle relative to axis A. However, it is contemplated that this configuration may be reversed. That is, the openings 40 that extend at an acute angle relative to axis A may be positioned proximally of the openings 40 that extend perpendicular to axis A. It is further contemplated that the openings 40 that extend at an acute angle relative to axis A may alternate with the openings 40 that extend perpendicular to axis A. It is envisioned that openings 40 may be disposed through angular ranges in various orientations relative to axis A, such as, for example, transverse or perpendicular and/or other angular orientations such as acute or obtuse, and/or may be offset or staggered. In some embodiments, openings 40 and/or pins/K-wires 46 may be rough, textured, porous, semi-porous, dimpled and/or polished to facilitate engagement between openings 40 and pins/K-wires 46.

End 36 includes an inner surface 48 defining a conduit 50 extending transverse to axis A. Conduit 50 includes a first portion 52 and a second portion 54 extending through end 36. Portion 54 defines a first chamber 56 having a hemispherical configuration and extending transverse to axis A. Portion 52 is tapered between a first end 58 defined by surface 42 and a second end 60, portion 54 extending from end 60. It is envisioned that all or only a portion of chamber 56 may be variously configured and dimensioned, such as, for example, planar, concave, convex, spherical, polygonal, irregular, uniform, non-uniform, staggered, tapered, consistent or variable, depending on the requirements of a particular application. It is further envisioned that portion 52 and/or chamber 56 may extend through end 36 at alternate orientations relative to axis A, such as, for example, transverse, perpendicular and/or other angular orientations such as acute or obtuse and/or may be offset or staggered and/or may be disposed at alternative angular orientations relative to axis A, depending on the requirements of a particular application. An outer surface of end 36 includes a threaded portion 62 configured to engage threads of a cap 64 to engage cap 64 with member 34.

Cap 64 has an inner surface 66 including a threaded first section 68 configured to engage portion 62 and a second section 70 defining a second chamber 72 having a hemispherical configuration and extending transverse to axis A. Chamber 72 is in communication with chamber 56 when portion 62 engages section 68 to engage cap 64 with member 34 such that chamber 56 is continuous with chamber 72. Chambers 56, 72 define a spherical cavity 74 when chamber 56 is continuous with chamber 72. Section 70 includes a projection 76 disposed circumferentially about surface 66 and extending parallel to axis A. Projection 76 is configured to engage a pivoting member 78 and includes a planar end face 90 extending perpendicular to axis A. It is envisioned that all or only a portion of chamber 72, cavity 74 or projection 76 may be variously configured and dimensioned, such as, for example, planar, concave, convex, spherical, polygonal, irregular, uniform, non-uniform, staggered, tapered, consistent or variable, depending on the requirements of a particular application. It is further envisioned that chamber 72 may extend through end cap 64 and/or that face 98 may be disposed at alternate orientations relative to axis A, such as, for example, transverse, perpendicular and/or other angular orientations such as acute or obtuse and/or may be offset or staggered and/or may be disposed at alternative angular orientations relative to axis A, depending on the requirements of a particular application. It is contemplated that cap 64 may engage member 34 in alternate fixation configurations, such as, for example, friction fit, pressure fit, locking protrusion/recess, locking keyway and/or adhesive.

Pivoting member 78 is movably disposed in cavity 74 and includes an inner surface 80 defining a passageway 82. Member 78 further includes a first end comprising a ball 84 having a substantially spherical configuration, a second end comprising a collet 86 having a cylindrical configuration and a recess 88 positioned between ball 84 and collet 86. Recess 88 is concave, extends parallel to axis A and is configured for disposal of projection 76 when cap 64 engages member 34. In one embodiment, member 78 is made of a deformable material to facilitate engagement of projection 76 with recess 88. It is envisioned that all or only a portion of recess 88 may be variously configured and dimensioned, such as, for example, planar, concave, convex, polygonal, irregular, uniform, non-uniform, staggered, tapered, consistent or variable, depending on the requirements of a particular application. It is further envisioned that recess 88 may be disposed at alternate orientations relative to axis A, such as, for example, transverse, perpendicular and/or other angular orientations such as acute or obtuse and/or may be offset or staggered and/or may be disposed at alternative angular orientations relative to axis A, depending on the requirements of a particular application.

When portion 62 fully engages section 68 to engage cap 64 with member 34, projection 76 is disposed in recess 88 to prevent member 78 from moving relative to cap 64 in the direction shown by arrow B or arrow BB. Disposing projection 76 in recess 88 also fixes member 78 in cavity 74 such that passageway 82 extends in a direction that is perpendicular to axis A. End 36 includes a flange 96 extending parallel to axis A and cap 64 includes an end face 100 extending parallel to axis A configured to engage flange 96 to prevent cap 64 from moving relative to end 36 in the direction shown by arrow BB past flange 96. In some embodiments, an outer surface of collet 86 includes an extension 102 extending parallel to axis A having a height that is greater than a height of an opening 104 defined by projection 76 such that extension 102 prevents collet 86 from moving through opening 104. That is, extension 102 prevents collet 86 from backing out of cavity 74 through opening 104. It is contemplated that all or only a portion of flange 96, face 100 and/or extension 102 may be variously configured and dimensioned, such as, for example, oval, oblong, square, rectangular, polygonal, irregular, uniform, non-uniform, offset, staggered, tapered, consistent or variable, depending on the requirements of a particular application. It is further contemplated that passageway 86 may be disposed at alternate orientations relative to axis A, such as, for example, transverse and/or other angular orientations such as acute or obtuse and/or may be offset or staggered and/or may be disposed at alternative angular orientations relative to axis A, depending on the requirements of a particular application.

A second member, such as, for example, a cannula 90 is disposed within passageway 82 such that cannula 90 also extends in a direction that is perpendicular to axis A. In embodiments in which passageway 82 is disposed transverse and/or at an acute angle relative to axis A, cannula 90 will also be disposed transverse and/or at an acute angle relative to axis A. Cannula 90 has an inner surface 92 defining a second passageway 94 configured for disposal of an inflatable bone tamp or a bone void filler so as to deliver the inflatable bone tamp or bone void filler through cannula 90 to a location adjacent a surgical site, such as, for example, a bone defect. Passageway 94 has a cylindrical cross section defining a uniform diameter along the length of cannula 90. It is envisioned that all or only a portion of passageway 94 may have alternate cross section configurations, such as, for example, oval, oblong, triangular, square, polygonal, irregular, uniform, non-uniform, offset, staggered, undulating, arcuate, variable and/or tapered.

In assembly, operation and use, system 30 is employed with a surgical procedure, such as, for a correction or treatment of a bone defect, such as, for example, a fracture. It is contemplated that one or all of the components of system 30 can be delivered or implanted as a pre-assembled device or can be assembled in situ. System 30 may be completely or partially revised, removed or replaced. For example, system 30 can be employed with a surgical correction treatment of an applicable condition or injury of an affected portion of a patient, such as, for example, a distal radius or a vertebra. It is envisioned that system 30 may also be used to treat other affected portions of the patient, such as, for example, a calcaneus bone, bones of the feet or hands, bones of the legs, etc.

In use, to treat a fracture, a medical practitioner obtains access to a surgical site including the fractured bone in any appropriate manner, such as through incision and retraction of tissues. In one embodiment, a drill is employed to remove bone tissue to provide access to a repair site. It is envisioned that system 30 can be used in any existing surgical method or technique including open surgery, mini-open surgery, minimally invasive surgery and percutaneous surgical implantation, whereby the fractured or injured bone is accessed through a mini-incision or sleeve that provides a protected passageway to the area. Once access to the surgical site is obtained, the particular surgical procedure can be performed for treating the injury or disorder. The configuration and dimension of system 30 is determined according to the configuration, dimension and location of a selected section of the bone fracture and the requirements of a particular application.

An incision is made in the body of a patient and a cutting instrument (not shown) creates a surgical pathway for implantation of components of system 30. This may include the use of a cannula or other device. A preparation instrument (not shown) can be employed to prepare tissue surfaces, as well as for aspiration and irrigation of a surgical region according to the requirements of a particular surgical application.

Pins/K-wires 46 are positioned within through openings 40 and are disposed in the anatomy of the patient, such as, for example, tissue, to fix or stabilize device 32 relative to the anatomy of the patient. Device 32 is stabilized with pins/K-wires 46 such that cannula 90 is positioned adjacent the bone disorder.

An inflatable bone tamp may be delivered through cannula 90 to a location adjacent the bone disorder or defect. The inflatable bone tamp may then be expanded to create a cavity or void in the bone by delivering a material, such as, for example, saline, a contrast solution or compressed air into an expandable member of the inflatable bone tamp, such as, for example, a balloon, to move the balloon from an unexpanded configuration to an expanded configuration. As the balloon moves from the unexpanded configuration to the expanded configuration, the balloon creates a void in the bone having the defect or disorder. Device 32 maintains cannula 90 in a stabilized orientation with respect to the body such that a single practitioner can insert the inflatable bone tamp through cannula 90 and operate the inflatable bone tamp in a steady manner.

After the void is formed in the bone, the inflatable bone tamp is removed from cannula 90. Bone filler material is then delivered through cannula 90 or a separate delivery tool configured to deliver bone filler material disposed in passageway 82 and into the void so as to at least partially fill the void and realign fragments of the fracture and/or elevate collapsed bone to its proper height. Device 32 maintains cannula 90 in a stabilized orientation with respect to the body such that a single practitioner can administer the bone filler material in a steady manner. It is envisioned that the bone filler material may include autograft, allograft, demineralized bone matrix, mineral composites, blocks, granules and pellets and bone cement, such as, for example, polymethylmethacrylate (PMMA)-based material (Kyphon HV-R, ActivOs, ActivOs 10, Xpede), calcium phosphate (Skaffold, Norian, Hydroset, KyphOs FS) and calcium sulfate (OsteoSet), as well as other injectables.

In one embodiment, system 30 includes an agent, which may be disposed, packed or layered within, on or about the components and/or surfaces of the components of system 30, such as, for example, device 32. It is envisioned that the agent may include bone growth promoting material, such as, for example, bone graft to enhance fixation of the fixation elements with the bone in need of repair. It is further contemplated that the agent may include therapeutic polynucleotides or polypeptides. It is further contemplated that the agent may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as HA, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines. The components of system 30 can be made of radiolucent materials such as polymers. Radiomarkers may be included for identification under x-ray, fluoroscopy, CT or other imaging techniques. It is envisioned that the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto. The embodiments above can also be modified so that some features of one embodiment are used with the features of another embodiment. One skilled in the art may find variations of these embodiments, which, nevertheless, fall within the spirit of the present disclosure, whose scope is defined by the claims set forth below.

What is claimed is:

1. A device for holding a surgical tool comprising:
   a first member extending along a longitudinal axis between a first end and a second end, the first end including an inner surface defining a conduit extending transverse to the longitudinal axis, the conduit including a first portion and a second portion defining a first chamber;
   a cap having an inner surface including a first section configured to engage an outer surface of the first member and a second section defining a second chamber extending transverse to the longitudinal axis, the second chamber being in communication with the first chamber when the cap engages the first member such that the first and second chambers define a cavity;
   a pivoting member movably disposed in the cavity and including an inner surface defining a passageway; and
   a second member disposed within the passageway,
   wherein the pivoting member includes a first end comprising a ball and a second end comprising a collet, the pivoting member having a recess between the ball and the collet, the second section including a projection extending parallel to the longitudinal axis, the projection being disposed in the recess when the cap engages the first member.

2. A device according to claim 1, wherein the first and second chambers each have a hemispherical configuration.

3. A device according to claim 1, wherein the first chamber is continuous with the second chamber when the cap engages the first member.

4. A device according to claim 1, wherein the cavity is substantially spherical when the cap engages the first member.

5. A device according to claim 1, wherein the pivoting member comprises a deformable material.

6. A device according to claim 1, wherein the outer surface of the first member and the first section are threaded, the threads on the outer surface of the first member being configured to engage the threads on the first section to engage the cap with the first member.

7. A device according to claim 1, wherein the second chamber extends through the inner surface of the cap and an outer surface of the cap.

8. A device according to claim 1, wherein the outer surface of the first member defines a flange extending parallel to the longitudinal axis and the cap includes an end face extending parallel to the longitudinal axis, the end face being configured to engage the flange to limit movement of the cap relative to the first member in a first direction.

9. A device for holding a surgical tool comprising:
   a first member extending along a longitudinal axis between a first end and a second end the first end including an inner surface defining a conduit extending transverse to the longitudinal axis the conduit including a first portion and a second portion defining a first chamber;
   a cap having an inner surface including a first section configured to engage an outer surface of the first member and a second section defining a second chamber extending transverse to the longitudinal axis, the second chamber being in communication with the first chamber when the cap engages the first member such that the first and second chambers define a cavity;
   a pivoting member movably disposed in the cavity and including an inner surface defining a passageway; and
   a second member disposed within the passageway,
   wherein the second member includes an inner surface defining a second passageway, the second passageway having an inflatable bone tamp disposed therein.

10. A device according to claim 9, wherein the pivoting member includes a first end comprising a ball and a second end comprising a collet.

11. A device for holding a surgical tool comprising:
    a first member extending along a longitudinal axis between a first end and a second end, the first end including an inner surface defining a conduit extending transverse to the longitudinal axis conduit including a first portion and a second portion defining a first chamber;
    a cap having an inner surface including a first section configured to engage an outer surface of the first member and a second section defining a second chamber extending transverse to the longitudinal axis, the second chamber being in communication with the first chamber when the cap engages the first member such that the first and second chambers define a cavity;
    a pivoting member movably disposed in the cavity and including an inner surface defining a passageway; and
    a second member disposed within the passageway, wherein the second member includes an inner surface defining a second passageway, the second passageway having a bone void filler disposed therein.

12. A device for holding a surgical tool comprising:
a first member extending along a longitudinal axis between a first end and a second end, the first end including an inner surface defining a conduit extending transverse to the longitudinal axis, the conduit including a first portion and a second portion defining a first chamber;
a cap having an inner surface including a first section configured to engage an outer surface of the first member and a second section defining a second chamber extending transverse to the longitudinal axis, the second chamber being in communication with the first chamber when the cap engages the first member such that the first and second chambers define a cavity;
a pivoting member movably disposed in the cavity and including an inner surface defining a passageway; and
a second member disposed within the passageway,
wherein the first portion is tapered between a first end and a second end, the second portion extending from the second end of the first portion.

13. A device for holding a surgical tool comprising:
a first member extending along a longitudinal axis between a first end and a second end, the first end including an inner surface defining a conduit extending transverse to the longitudinal axis, the conduit including a first portion and a second portion defining a first chamber;
a cap having an inner surface including a first section configured to engage an outer surface of the first member and a second section defining a second chamber extending transverse to the longitudinal axis, the second chamber being in communication with the first chamber when the cap engages the first member such that the first and second chambers define a cavity;
a pivoting member movably disposed in the cavity and including an inner surface defining a passageway; and
a second member disposed within the passageway,
wherein the pivoting member includes a first end comprising a ball and a second end comprising a collet, the collet including an outer surface having a projection extending therefrom configured to prevent the collet from backing out of the second chamber.

14. A device according to claim 13, wherein the projection is disposed circumferentially about the outer surface of the collet.

15. A device for holding a surgical tool comprising:
a first member extending along a longitudinal axis between a first end and a second end, the first end including an inner surface defining a conduit extending transverse to the longitudinal axis, the conduit including a first portion and a second portion defining a first chamber having a hemispherical configuration, the first portion being tapered between a first end and a second end, the second portion extending from the second end of the first portion;
a cap having an inner surface including a threaded first section configured to engage a threaded outer surface of the first member and a second section defining a second chamber having a hemispherical configuration and extending transverse to the longitudinal axis, the second chamber being in communication with the first chamber when the cap engages the first member such that the first chamber is continuous with the second chamber and the first and second chambers define a spherical cavity, the second section including a projection extending parallel to the longitudinal axis;
a pivoting member movably disposed in the cavity and including an inner surface defining a passageway, the pivoting member including a first end comprising a ball, a second end comprising a collet and a recess between the ball and the collet configured for disposal of the projection when the cap engages the first member; and
a second member disposed within the passageway, the second member including an inner surface defining a second passageway having an inflatable bone tamp or a bone void filler disposed therein.

* * * * *

UNITED STATES PATENT AND TRADEMARK OFFICE
CERTIFICATE OF CORRECTION

Page 1 of 1

PATENT NO. : 9,161,818 B2
APPLICATION NO. : 13/798320
DATED : October 20, 2015
INVENTOR(S) : Arthur et al.

It is certified that error appears in the above-identified patent and that said Letters Patent is hereby corrected as shown below:

On the title page item (74), under "Attorney, Agent, or Firm", in Column 2, Lines 1-2, delete "Sorell Lenna & Schmidt LLP" and insert -- Sorell, Lenna & Schmidt, LLP --, therefor.

In the specification,

In Column 5, Line 37, delete "polycaroplaetohe" and insert -- polycaprolactone --, therefor.

In Column 6, Line 47, delete "face 90" and insert -- face 98 --, therefor.

In Column 7, Lines 40-41, delete "passageway 86" and insert -- passageway 82 --, therefor.

In the claims,

In Column 10, Line 31, in Claim 9, delete "second end" and insert -- second end, --, therefor.

In Column 10, Line 33, in Claim 9, delete "axis" and insert -- axis, --, therefor.

In Column 10, Line 56, in Claim 11, delete "axis" and insert -- axis, --, therefor.

In Column 11, Line 28, in Claim 13, delete "chamber:" and insert -- chamber; --, therefor.

Signed and Sealed this
Twenty-ninth Day of March, 2016

Michelle K. Lee
*Director of the United States Patent and Trademark Office*